(12) United States Patent
Smith

(10) Patent No.: US 11,860,197 B2
(45) Date of Patent: Jan. 2, 2024

(54) LEAKAGE CURRENT MANAGEMENT SYSTEMS, DEVICES, AND METHODS

(71) Applicant: NxStage Medical, Inc., Lawrence, MA (US)

(72) Inventor: Mark F. Smith, Lawrence, MA (US)

(73) Assignee: NxStage Medical, Inc., Lawrence, MA (US)

(*) Notice: Subject to any disclaimer, the term of this patent is extended or adjusted under 35 U.S.C. 154(b) by 33 days.

(21) Appl. No.: 17/529,819

(22) Filed: Nov. 18, 2021

(65) Prior Publication Data

US 2022/0196708 A1 Jun. 23, 2022

Related U.S. Application Data

(60) Provisional application No. 63/129,370, filed on Dec. 22, 2020.

(51) Int. Cl.
*G01R 31/52* (2020.01)
*G01R 15/18* (2006.01)
(Continued)

(52) U.S. Cl.
CPC ........... *G01R 15/18* (2013.01); *A61M 1/3669* (2013.01); *A61N 1/16* (2013.01); *G01R 19/145* (2013.01); *G01R 31/52* (2020.01)

(58) Field of Classification Search
CPC ...... G01R 15/18; G01R 15/185; G01R 31/52; G01R 19/145; A61M 1/3669; A61N 1/16
See application file for complete search history.

(56) References Cited

U.S. PATENT DOCUMENTS 2,709,785 A * 5/1955 Fielden ................. G01N 27/025
324/695
3,015,061 A * 12/1961 Boeke .................... G01N 27/74
324/204
(Continued)

FOREIGN PATENT DOCUMENTS

CN 103328960 A * 9/2013 ........... G01N 27/023
JP S54173921 U 12/1979
(Continued)

OTHER PUBLICATIONS

International Search Report and Written Opinion dated Mar. 14, 2022 for International Patent Application No. PCT/US2021/059885.
(Continued)

*Primary Examiner* — Patrick Assouad
*Assistant Examiner* — Demetrius R Pretlow
(74) *Attorney, Agent, or Firm* — Potomac Law Group, PLLC

(57) ABSTRACT

A sensor/transducer for use in reducing leakage current from a patient fluidly connected to a medical device by tubing filled with a conductive fluid (e.g., blood or dialysate (a "fluid line")) includes a magnetically conductive core with 1) a centrally located support for a coil of fluid line, and 2) coiled electrical conductors located at positions that are spaced from the centrally located support, on opposite sides of the centrally located support. The sensor/transducer can be used to measure leakage current carried by the conductive fluid in the fluid line, or it can be used to induce current in the fluid line in a manner that reduces the leakage current.

19 Claims, 12 Drawing Sheets

(51) Int. Cl.
*A61M 1/36* (2006.01)
*A61N 1/16* (2006.01)
*G01R 19/145* (2006.01)

(56) References Cited

U.S. PATENT DOCUMENTS

| | | | | |
|---|---|---|---|---|
| 3,396,331 | A * | 8/1968 | Sperry, III | G01N 27/025 |
| | | | | 324/445 |
| 3,867,688 | A * | 2/1975 | Koski | G01N 27/023 |
| | | | | 324/696 |
| 4,155,852 | A | 5/1979 | Fischel et al. | |
| 4,540,942 | A * | 9/1985 | Yamamura | G05D 1/0206 |
| | | | | 405/160 |
| 4,579,137 | A * | 4/1986 | Brandt, Jr. | F15B 5/003 |
| | | | | 251/129.08 |
| 5,089,781 | A * | 2/1992 | Arichika | G01R 27/22 |
| | | | | 324/204 |
| 5,268,642 | A * | 12/1993 | Uchidomi | G01N 27/023 |
| | | | | 250/551 |
| 5,325,728 | A | 7/1994 | Zimmerman et al. | |
| 5,631,552 | A * | 5/1997 | Ogawa | G01F 1/7046 |
| | | | | 73/19.1 |
| 5,935,077 | A * | 8/1999 | Ogle | A61B 5/0265 |
| | | | | 73/861.12 |
| 5,942,893 | A * | 8/1999 | Terpay | H01F 27/36 |
| | | | | 336/84 R |
| 5,959,455 | A * | 9/1999 | Brown | G01N 27/023 |
| | | | | 324/695 |
| 6,626,048 | B1 * | 9/2003 | Dam Es | G01F 1/586 |
| | | | | 73/861.15 |
| 7,323,964 | B1 * | 1/2008 | Shyu | H01F 38/14 |
| | | | | 336/131 |
| 10,912,877 | B2 | 2/2021 | Fabig et al. | |
| 2007/0018659 | A1 * | 1/2007 | Homan | E21B 49/10 |
| | | | | 324/693 |
| 2008/0065006 | A1 | 3/2008 | Roger et al. | |
| 2008/0101099 | A1 * | 5/2008 | Jacobs | H02M 1/14 |
| | | | | 363/47 |
| 2008/0128134 | A1 * | 6/2008 | Mudunuri | C10G 1/02 |
| | | | | 166/302 |
| 2010/0185132 | A1 | 7/2010 | Han et al. | |
| 2012/0223795 | A1 * | 9/2012 | Hester | H01F 27/324 |
| | | | | 336/90 |
| 2013/0099808 | A1 * | 4/2013 | Li | G01N 27/06 |
| | | | | 324/722 |
| 2014/0031736 | A1 * | 1/2014 | Wright | A61M 1/3462 |
| | | | | 604/500 |
| 2015/0348701 | A1 * | 12/2015 | Rezanezhad Gatabi | H01F 27/2823 |
| | | | | 324/691 |
| 2016/0334352 | A1 * | 11/2016 | Fougere | G01N 9/00 |
| 2018/0074105 | A1 * | 3/2018 | Horanoff | G01R 31/54 |
| 2019/0082975 | A1 * | 3/2019 | Sano | G01R 19/16576 |
| 2020/0030517 | A1 | 1/2020 | Basati et al. | |
| 2021/0293895 | A1 * | 9/2021 | Essawy | G01R 31/52 |
| 2022/0163484 | A1 * | 5/2022 | Yamada | G01N 27/904 |

FOREIGN PATENT DOCUMENTS

| | | |
|---|---|---|
| JP | H10185962 A | 7/1998 |
| JP | 2000331840 A | 11/2000 |

OTHER PUBLICATIONS

International Search Report and Written Opinion dated Dec. 16, 2021, issued in International Application No. PCT/US2021/041617.

\* cited by examiner

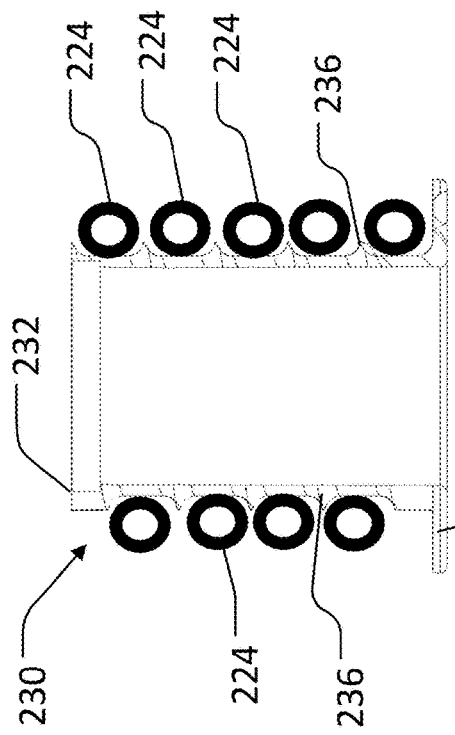
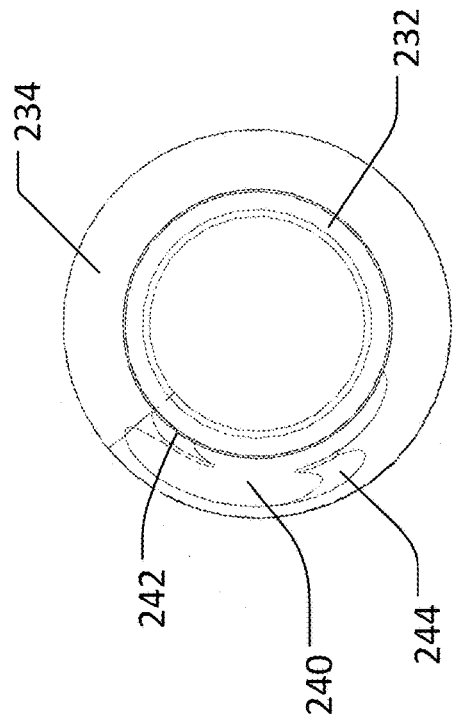
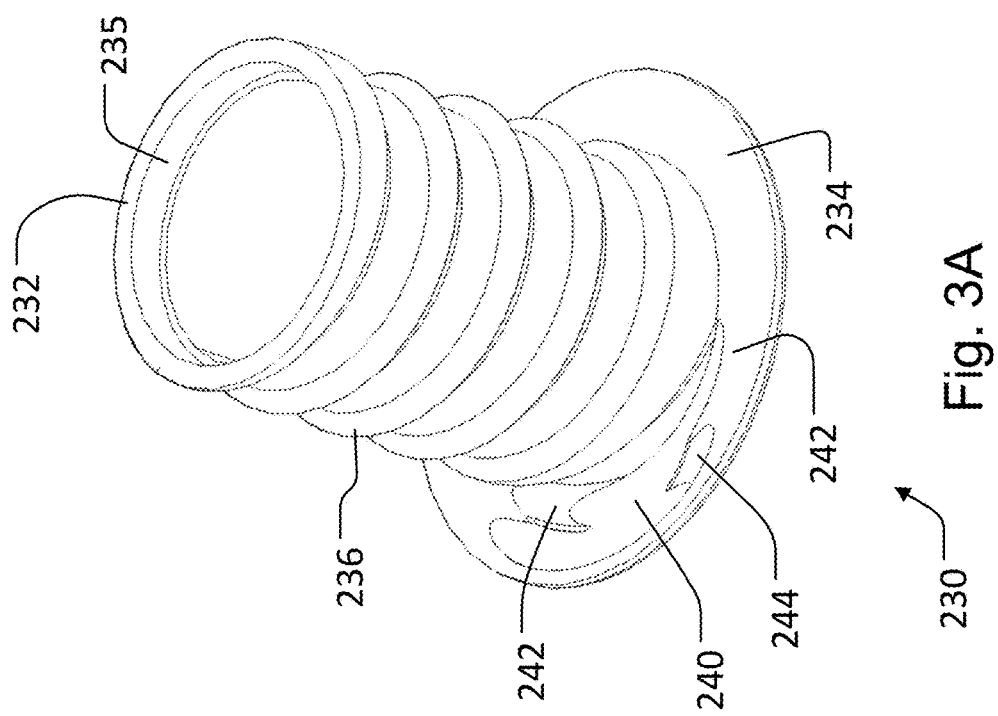
Fig. 3B
Fig. 3C
Fig. 3A

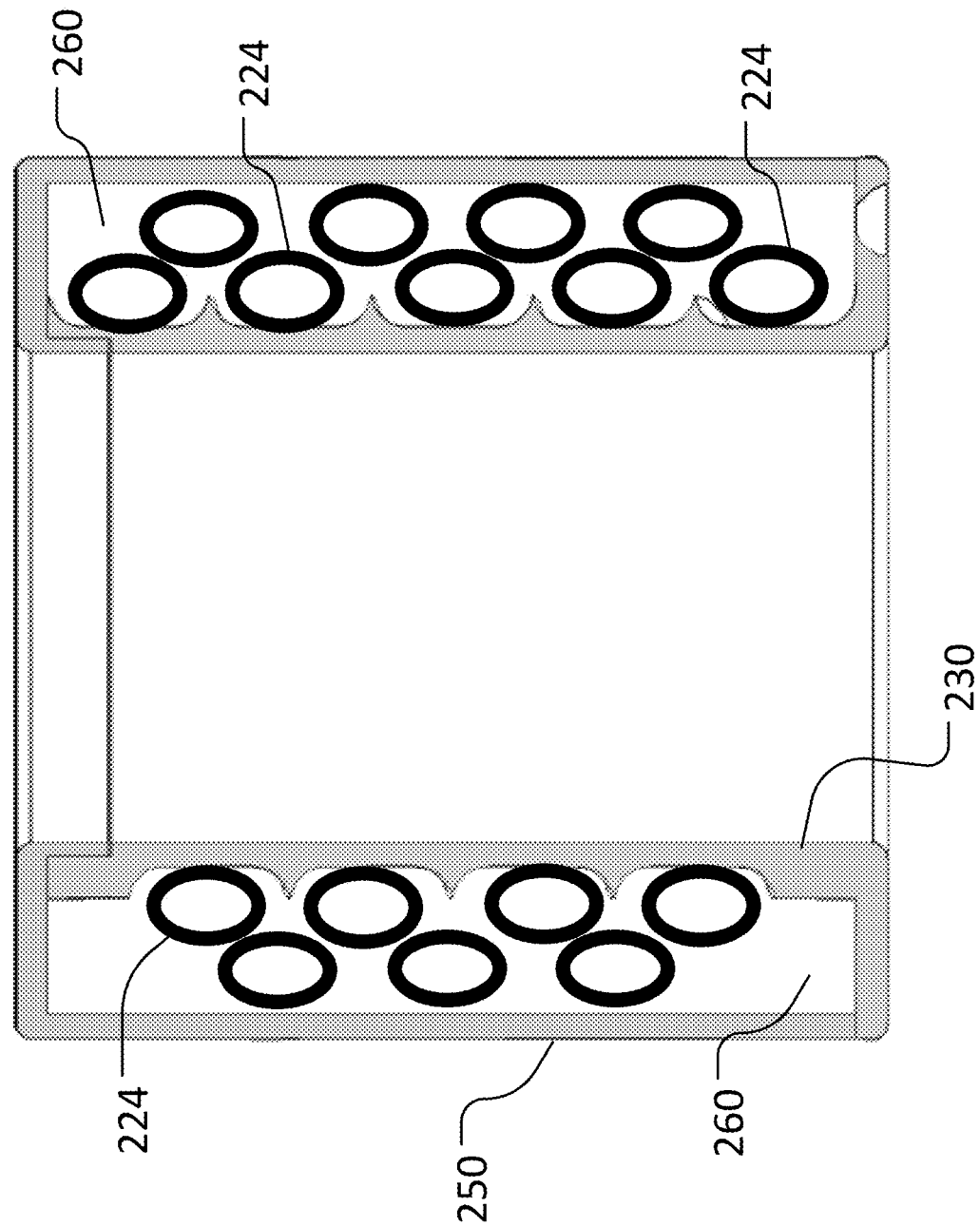

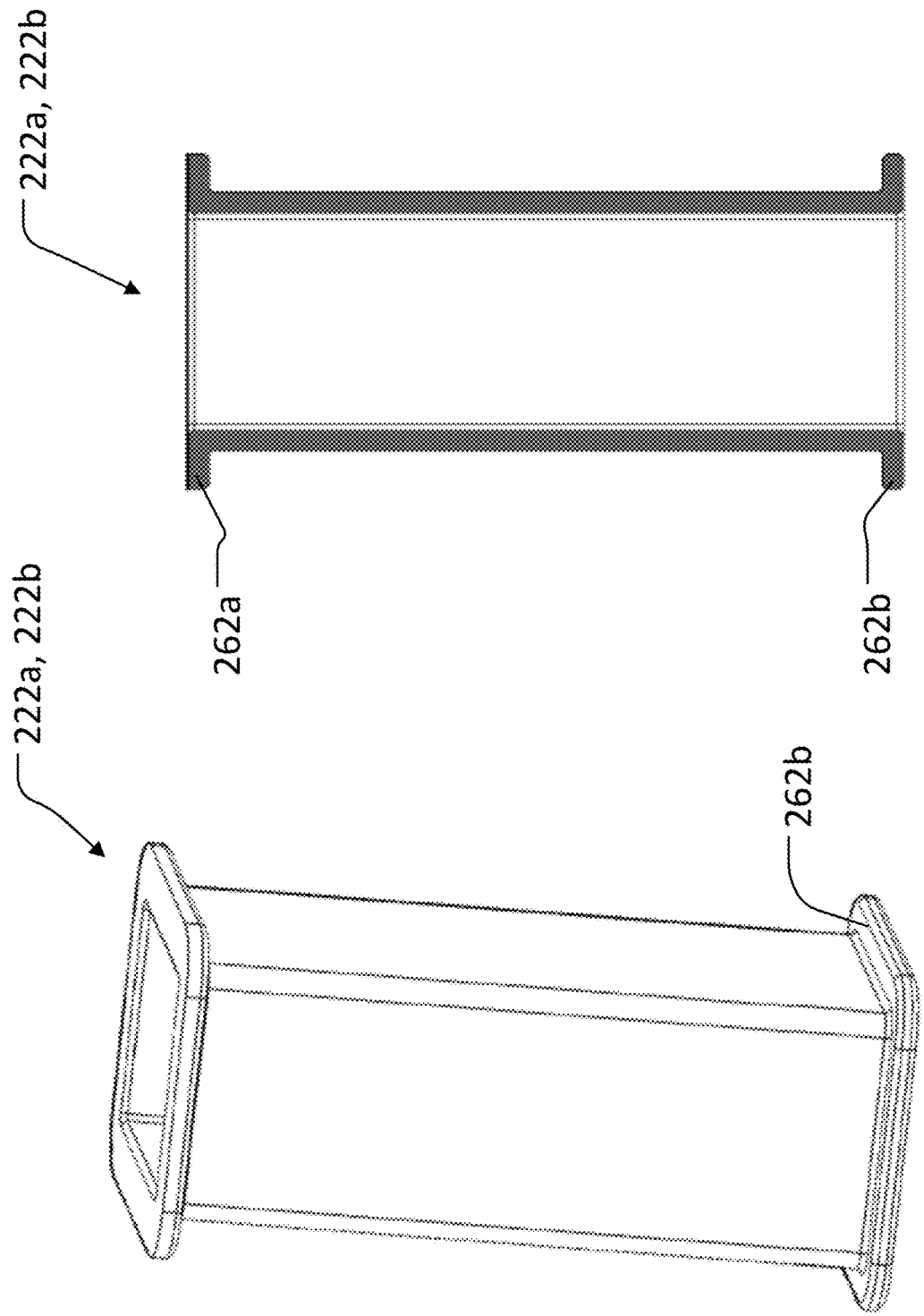

LEAKAGE CURRENT MANAGEMENT SYSTEMS, DEVICES, AND METHODS

CROSS-REFERENCE TO RELATED APPLICATIONS

This application claims priority to and the benefit of U.S. Provisional Patent Application No. 63/129,370 filed Dec. 22, 2020, which is hereby incorporated by reference in its entirety.

BACKGROUND

The use of electrically powered medical devices or equipment connected to a patient is very common in modern medicine. Along with the benefits these devices are designed to bring to a patient, they also can create a potential hazard of electric shock to the patient. Electric shock can be caused by current (referred to as leakage current) flowing through the patient's heart, for instance, creating ventricular defibrillation, which a medical device may induce in an earthed patient or sink to earth if the patient is in contact with another source of electricity. It is desirable to design medical equipment to reduce leakage current.

SUMMARY

When an alternating current (AC) is flowing in a conductive path, which could be a fluid line filled with conductive fluid, the fluid line may be capacitively coupled to a conductive surface next to or near the fluid line. When the fluid line is part of a medical equipment that is coupled to a patient and the conductive surface is at ground potential, the capacitive coupling of the fluid line could cause leakage current to flow through the patient when the patient is electrified with alternating current.

Some embodiments of the disclosure describe a leakage current canceling transducer and sensor used for cancellation of leakage current. The leakage current from a patient can be reduced by injecting alternating current into a blood line and thus inducting a voltage drop from the blood line entering the medical equipment under test (DUT). This induced voltage drop is intended to be similar in magnitude to the voltage at the patient relative to the DUT. If the injected alternating current is equal to or slightly less than the leakage current, then the leakage current will be reduced by the amount of the injection current. By adjusting the injected alternating current, the leakage current from the patient can be reduced to acceptable levels.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Some of the figures may have been simplified by the omission of selected features for the purpose of more clearly showing other underlying features. Such omissions of elements in some figures are not necessarily indicative of the presence or absence of particular elements in any of the exemplary embodiments, except as may be explicitly disclosed in the corresponding written description.

FIG. 3A is a perspective view from above of a fluid line spool that can be used in connection with the sensor/transducer illustrated in FIGS. 2A-C.

FIG. 3B is a schematic section view of the fluid line spool illustrating a fluid line coiled around the spool according to embodiments of the disclosed subject matter.

FIG. 3C is a plan view of the fluid line spool according to embodiments of the disclosed subject matter.

FIG. 5 is a section view schematically illustrating a coiled fluid line housed within the fluid line cassette according to embodiments of the disclosed subject matter.

FIGS. 6A and 6B are a perspective view slightly from above and a section view, respectively, of a coil-winding bobbin according to embodiments of the disclosed subject matter.

DETAILED DESCRIPTION

Figure 1A:
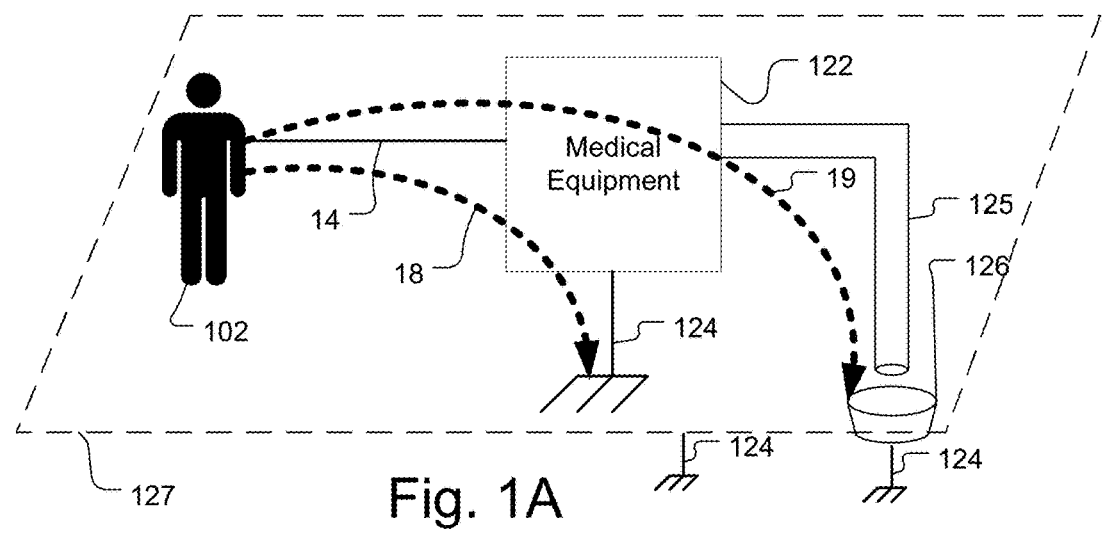
FIG. 1A illustrates an example of a patient connected to medical equipment according to embodiments of the disclosed subject matter.

Referring to FIG. 1A, a patient 102 is undergoing or about to undergo medical treatment by medical equipment 122. In an exemplary embodiment, medical equipment 122 is a blood treatment device, such that patient 102 is connected to the blood treatment device by one or more hollow fluid lines 14 that can convey blood and/or other fluids between the patient 102 and the blood treatment device. Although only a single line is illustrated, it is understood that the illustration represents one or more such lines. In various embodiments, medical equipment 122 may be a hemodialysis treatment device, a hemofiltration treatment device, and any other device that conveys blood and/or other fluids between the patient and the medical equipment 122. In some embodiments, medical equipment 122 is a peritoneal dialysis treatment device that is configured to pump dialysate into the patient's peritoneal cavity and to withdraw spent dialysate from the patient's peritoneal cavity and certain times and/or intervals.

It can be appreciated that the fluid line 14, when filled with a conductive fluid such as blood or dialysate, creates a conductive connection between the patient 102 and the medical equipment 122. This conductive connection creates a possibility of a leakage current 18 and/or 19 to flow between the patient 102 and ground 124, as shown in FIG. 1A. Leakage current 18 could flow from the patient 102 through the medical equipment 122 and to ground 124 via a ground connection between the medical equipment 122 and the ground 124, such as a ground connection as part of an electrical power connection. Alternatively, or additionally, leakage current 19 could flow from the patient to the medical equipment 122 and to ground 124 through another fluid connection of the medical equipment 122, such as a drain line 125. In some embodiments, the medical equipment 122 generates waste (e.g., spent dialysate fluid) that is discarded into a drain 126. The drain 126 may be itself at ground potential. For example, some drain plumbing is made of copper, which is highly conductive and is eventually in physical contact with earth ground. Thus, when a conductive fluid flows through drain line 125, there is a possibility of forming a conductive connection to ground 124 through drain 126. In some embodiments, drain line 125 is a hollow tube formed from an insulating material (e.g., PVC, rubber, plastic, etc.) and the floor 127 of the medical facility where the medical equipment 122 is used is made of metal or other conductive material. In this situation, the conductive fluid in drain line 125 could become capacitively coupled to the floor 127, which is at ground potential, thus creating yet another conductive path for leakage current 19.

Figure 1B:
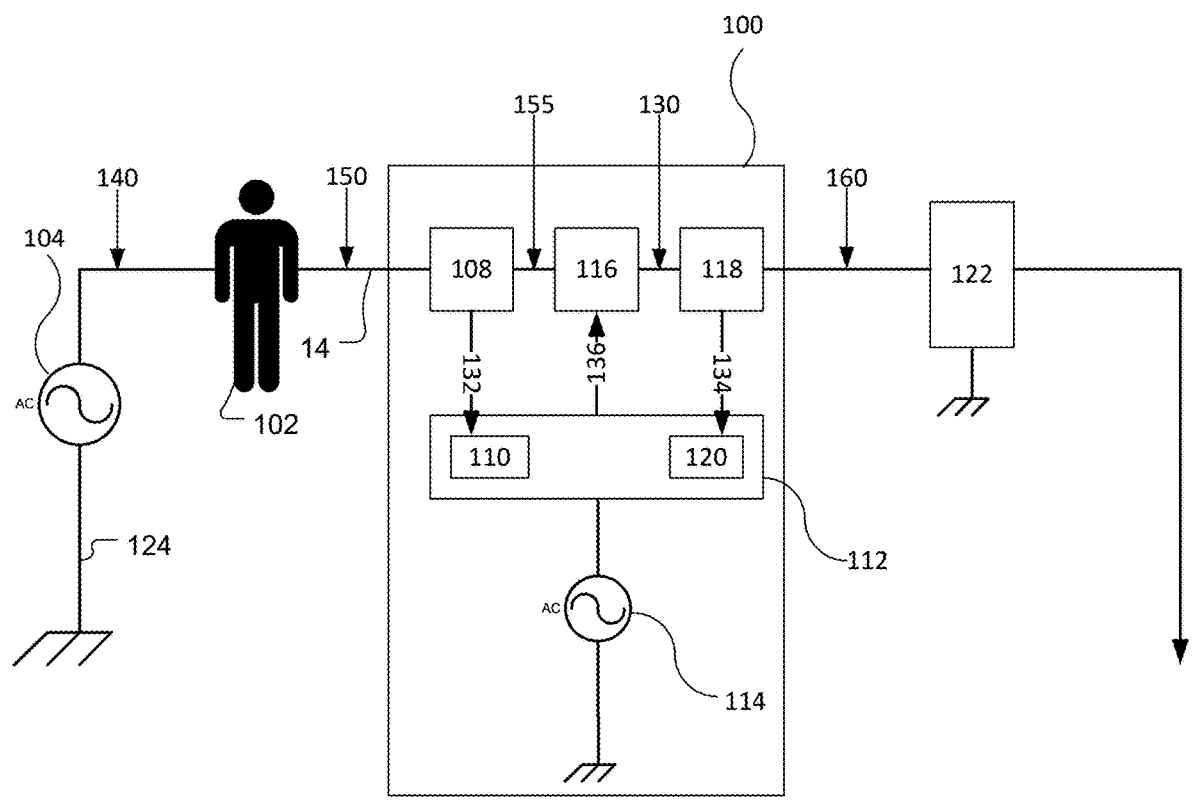
FIG. 1B illustrates a system for reducing leakage current according to embodiments of the disclosed subject matter.

Turning next to FIG. 1B, an example of the leakage current reduction system 100 is described. Embodiments of system 100 reduce current leakage from the patient (e.g., electrified patient) to the medical device by selectively injecting or inducing AC (alternating current) into the conductive fluid (e.g., blood lines) causing a voltage drop from the blood line entering the medical device. The AC is induced by transducer 116. In some embodiments, transducer 116 is contactless, while in other embodiments the transducer 116 may be a contact transducer.

A contactless transducer does not come into direct contact with the conductive fluid into which current is induced. Instead, the transducer generates a magnetic field, which in turn induces current in the fluid. Exemplary embodiments of such a transducer include a toroid that surrounds the fluid line 14 and/or 125 conveying conductive fluid. The toroid has wire windings on one or more sides thereof, and when current passes through the wire windings, a magnetic field is generated in the toroid. The magnetic field may be oriented circularly around the tube with conductive fluid, and it may induce an electrical current in the fluid.

A contact transducer is in direct contact with the conductive fluid, so that an electrical current can be injected into the fluid directly from the transducer. In embodiments, the contact transducer includes a conductive tube that is fluidly coupled to the fluid line (14 and/or 125) conveying conductive fluid. The fluid coupling can be achieved via a luer connector, or another similar coupling device. In this configuration, the conductive tube can be conductively connected to, and driven by, a controller to inject a specified current into the conductive fluid passing through the conductive tube.

If the current which is induced in or injected into the conductive fluid is substantially equal to or a threshold less than the leakage current (18, 19), the leakage current can be reduced by the degree of the injected or induced current. Other embodiments can selectively inject or induce any other suitable amount of current to reduce the current leakage from the patient to the medical device.

Referring still to FIG. 1B, patient 102 is illustrated as being connected to AC source 104 to represent a voltage of the patient. The patient 102 is further connected by a fluid line 14 to medical equipment 122. The leakage current reduction system 100 is illustrated as installed on fluid line 14, between the patient 102 and the medical equipment 122. However, system 100 can also be installed on drain line 125 in addition to, or instead of, on the fluid line 14.

The system 100 includes a proximal current sensor 108 and a distal current sensor 118, as shown in FIG. 1B. Both of the current sensors detect electrical current flowing through fluid line 14 (i.e., in the conductive fluid that flows through the fluid line 14). System 100 also includes a transducer 116 which is operatively coupled to transducer controller 112. The transducer controller 112 may include signal conditioners 110 and 120, as shown. The signal conditioners may amplify and/or filter the signal output from sensors 108 and 118. The transducer controller 112 is powered by a power supply 114.

In embodiments, only a single current sensor is used (not shown). In other embodiments, the distal current sensor 118 measures electrical current in fluid line 14. In embodiments, the distal current sensor 118 is a contactless sensor, similar to the transducer 116. For example, sensor 118 may have a generally toroidal shape with one or more wire windings, and be placed around the fluid line 14. In some embodiments, the toroid of sensor 118 may be a single piece, such that fluid line 14 will need to be inserted through the opening in the toroid. In other embodiments, the toroid may have an air gap which allows the toroid to open and close around fluid line 14. Further examples of embodiments of sensors 108 and 118 are described below.

Figure 1C:
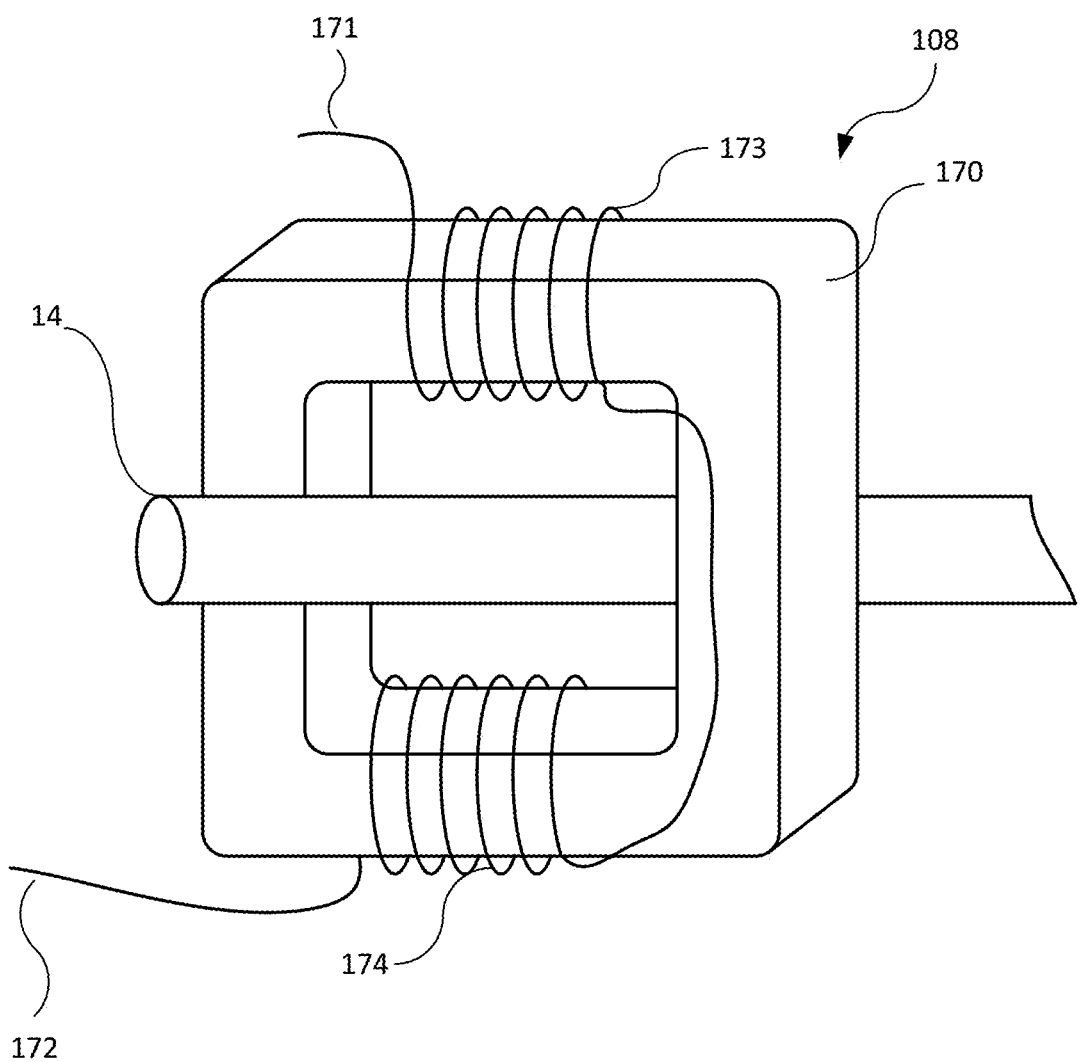
FIG. 1C illustrates a contactless current sensor or transducer according to embodiments of the disclosed subject matter.

Referring to FIG. 1C, an example of an embodiment of contactless current sensor 108, 118 is described. The sensor has a body 170 which has a toroidal shape, such that an opening in the center is surrounded by a material. The body 170 may be round, square, rectangular, oval, and may have rounded corners. An example of a square with rounded corners is illustrated. The body 170 can be made from a laminated material, such as Carpenter High Permeability 49 alloy ("Carpenter 49") which is a 48% nickel-iron alloy that has high saturation flux density, high magnetic permeability and low core loss.

Fluid line 14 is shown passing through the central opening of the toroidal shape, but it is understood that the sensor can be used on any fluid line (e.g., drain line 125) in addition or instead of fluid line 14. In some embodiments, multiple fluid lines may pass through the central opening at the same time (e.g., a venous blood line and an arterial blood line of a hemodialysis machine). A wire with a first winding 173 and a second winding 174 has ends 171 and 172. The two windings can be connected in series, as shown. In embodiments, the windings may be connected in parallel (not shown). When electrical current, such as alternating current is present in fluid line 14, it generates a magnetic field in the body 170, which in turn induces an electrical current in the wire of the two windings. Thus, a signal representative of the electrical current in the fluid line 14 can be output from ends 171 and 172, and supplied to the controller 112.

In embodiments, the body 170 is split into two halves by an air gap. An example of one half of the body 170 is shown in FIG. 21. It will be understood that the transducer 116 may have a similar or same design as the sensor 108. In embodiments, transducer 116 has four windings connected in series, each on one side of the body 170 (not shown).

In embodiments, the sensor 108, 118 is a contact sensor, such that it is in direct contact with the conductive fluid flowing through fluid line 14. It will be understood that sensor 108 can be the same as sensor 118, but does not need to be. In embodiments, one or both of the sensors 108 and 118 will be a contactless sensor. In embodiments, one or both of the sensors 108 and 118 will be a contact sensor. It will be further understood that contact sensors and contact free sensors can be combined with contact transducers and contactless transducers in all possible combinations.

In embodiments, the distal sensor 118 is used to drive the transducer 116, while the proximal sensor 108 is used as a safety measure to monitor the leakage current from patient 102 and thus verify the operation and status of system 100. In embodiments, the transducer 116 may have the same design as sensors 108 and 118. In some embodiments, one of the sensors 108 and 118 may be omitted.

Embodiments of system 100 can reduce the amount of leakage current when a patient is electrified (e.g., by AC mains). For example, a fault condition mitigated by embodiments is when patient 102 is accidentally connected to AC source 104 (e.g., AC mains). An issue can arise when electrical current flows from patient 102 to a low potential, such as earth ground 124. The current can flow from patient 102 to electrically coupled medical device 122 (e.g., a kidney dialysis machine) through a conductive fluid (e.g., fluid line 14) and out of medical device 122 to a drain. In this illustrative example, there are multiple current leakage paths to earth ground 124. Some of the leakage paths are in the medical device, another leakage path might be through the drain line to a conductive floor, and yet another leakage path might be the drain line emptying into a copper drain pipe.

Because of the potential fault and the multiple potential leakage current paths, various current mitigation techniques are disclosed. Embodiments utilize the fluid resistance (e.g., patient blood resistance) to assist in limiting the leakage current. A reduction to the voltage potential drop across the conductive fluid electrical resistance can achieve this objective. Referring back to FIG. 1C, if the patient voltage VP2 in fluid line 14 measured at location 150 and the voltage measured at location 160 are nearly the same voltage, then the current through the blood line is nearly zero. This can be achieved by measuring the current (and/or voltage) by sensors 108 and/or 118, and inducing an appropriate current in the fluid line 14 by transducer 116.

Embodiments inject current into the fluid line 14 (e.g., magnetically induce an alternating current via transducer 116) in phase with leakage current IPLC measured in the fluid line 14. The induced current can replace the leakage current into the machine and force VP2 to a voltage closer to VP1 measured at location 140, thus reducing leakage current IPLC measured at location 155.

Because embodiments of the design have reactive elements, capacitors and inductors, the phasing of the reducing current is non-trivial. Therefore, leakage current IPLC 130 is measured before and after transducer 116 by leakage current sensors 108 and 118. By using the before and after current signals, transducer controller 112 can adjust the phase to be in phase with the IPLC 130 current signal using power supply 114. For example, using the current sensed by leakage current sensors 108 and 118, sensor signal conditioners 110 and 120 can determine input leakage current voltage VCI 132 and output leakage current voltage VCO 136, and provide these voltages to transducer controller 112 such that an induced current IC 134 can be determined.

In some embodiments, the current sensed by leakage current sensor 108 can be controlled at or near a predefined threshold or range, such as 10 µA or 20 µA via transducer controller 112. The induced current IC 134 is injected into the fluid stream and summed with the patient leakage current IPLC 130. The resultant current is equal to the current that would have passed through the patient if the canceling transducer was not functional.

Another embodiment of a sensor/transducer 200 that may be used in connection with a leakage current-management system as described above is illustrated in FIGS. 2A-C, 3A-E, 4A-B, 5, 6A-C, 7, and 8A-B. Advantageously, identical sensor/transducers 200 may be used as 1) a leakage current-cancelling transducer 116 or as 2) a proximal current sensor 108 located upstream of the current-cancelling transducer 116 and/or a distal current sensor 118 located downstream of the current-cancelling transducer 116, which sense or senses the flow of current within the fluid lines. In the description below, reference is made to fluid line 224, but it should be appreciated that the sensor/transducer 200 can be used with an insulated wire wrapped in the manner of fluid line 224, without deviating from the concepts further described below, resulting in a high sensitivity current sensor.

In general, the embodiment of a sensor/transducer 200 may include an E-shaped core 202, which has outer arms 204a and 204b and a middle arm 206 all extending from a base portion 208 of the E-shaped core 202 as shown in FIGS. 2C, 7, and 8A-B in particular. For uniformity of performance of the sensor/transducer 200 regardless of how the sensor/transducer 200 is attached to a fluid line (as described further below), each of the longitudinal centerlines of the outer arms 204a and 204b may be the same distance from the longitudinal centerline of the middle arm 206, or the arms may be spaced apart from each other (204a to 206, 204b to 206) by distances that are not the same. Additionally, the outer arms 204a, 204b and the middle arm 206 may all extend the same distance from the base portion 208 to facilitate assembly of the sensor transducer 200, or they may extend by different distances.

Figure 7:
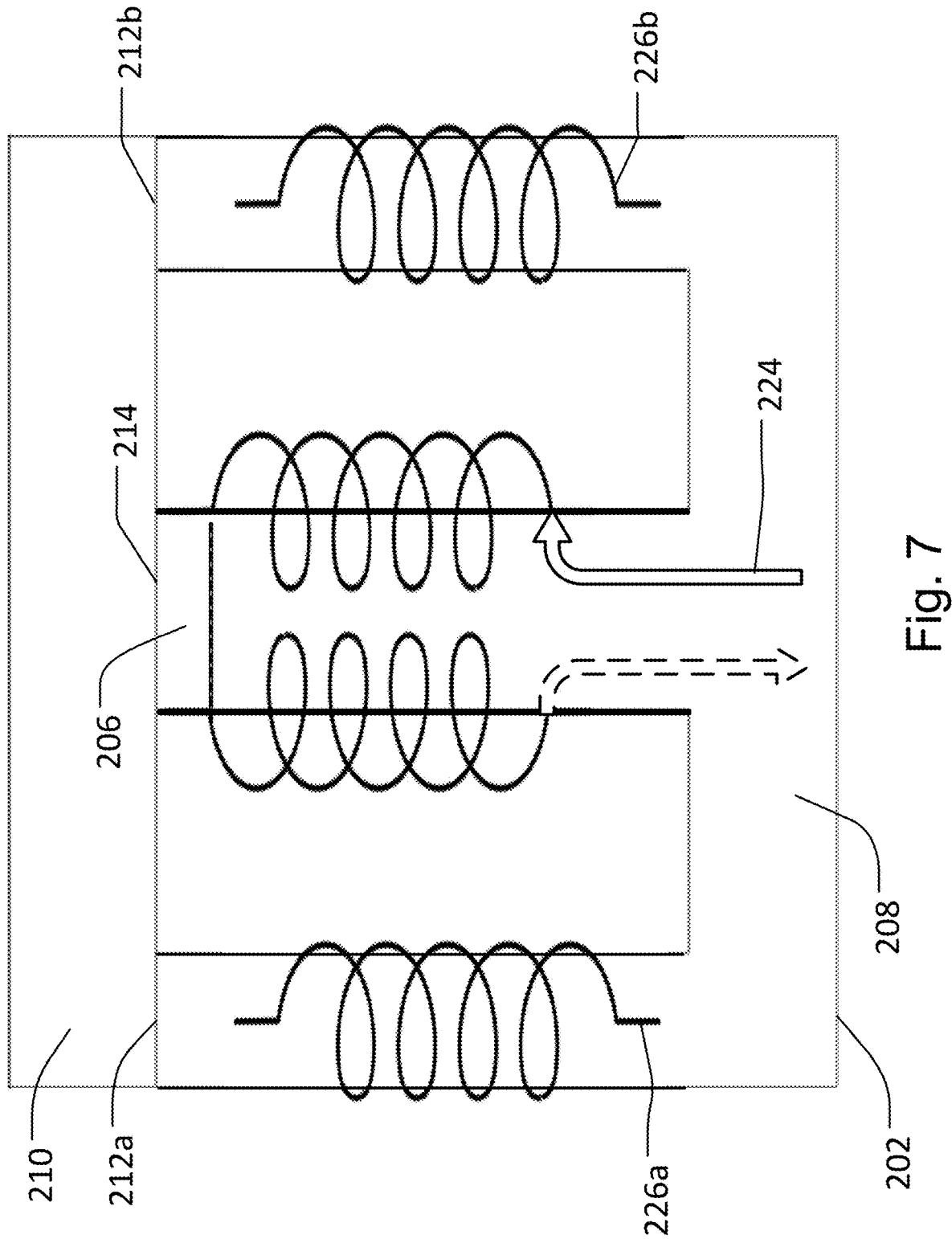
FIG. 7 is a schematic view illustrating how a fluid line and electrical conductors may be formed into coils and supported at respective locations within a sensor/transducer according to embodiments of the disclosed subject matter.
Figure 8A:
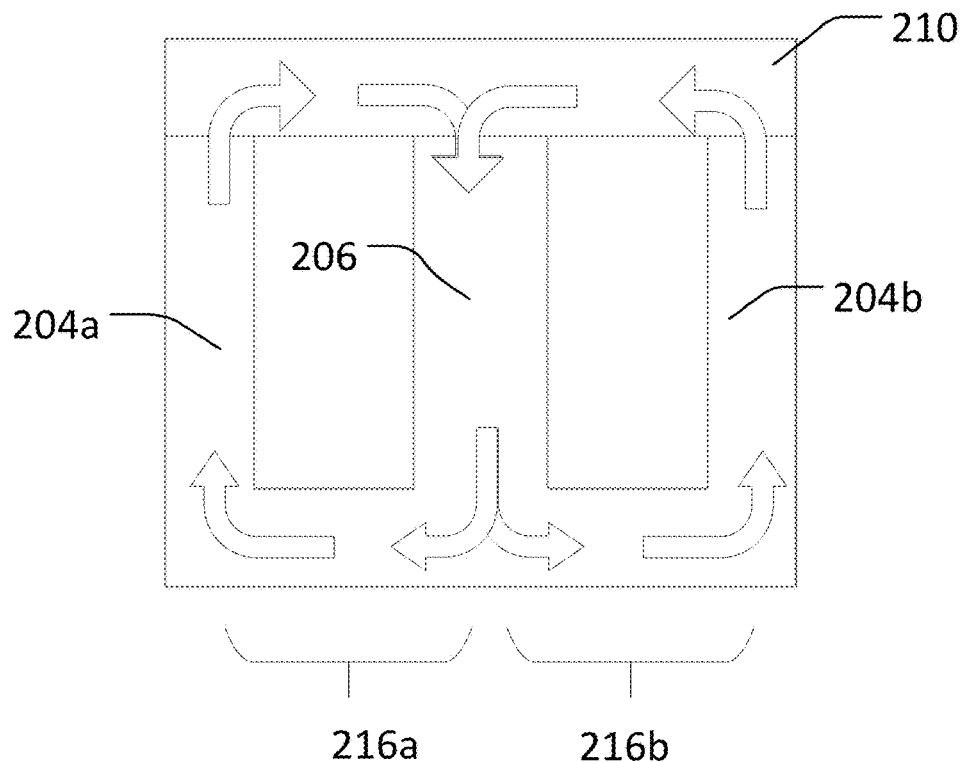
FIGS. 8A and 8B illustrate schematically magnetic circuits that are formed during use of the sensor/transducer illustrated in FIGS. 2A and 2B, and reversal of the magnetic circuits with alternating electrical currents in the fluid line and the electrical conductors illustrated in FIG. 7 according to embodiments of the disclosed subject matter.
Figure 8B:
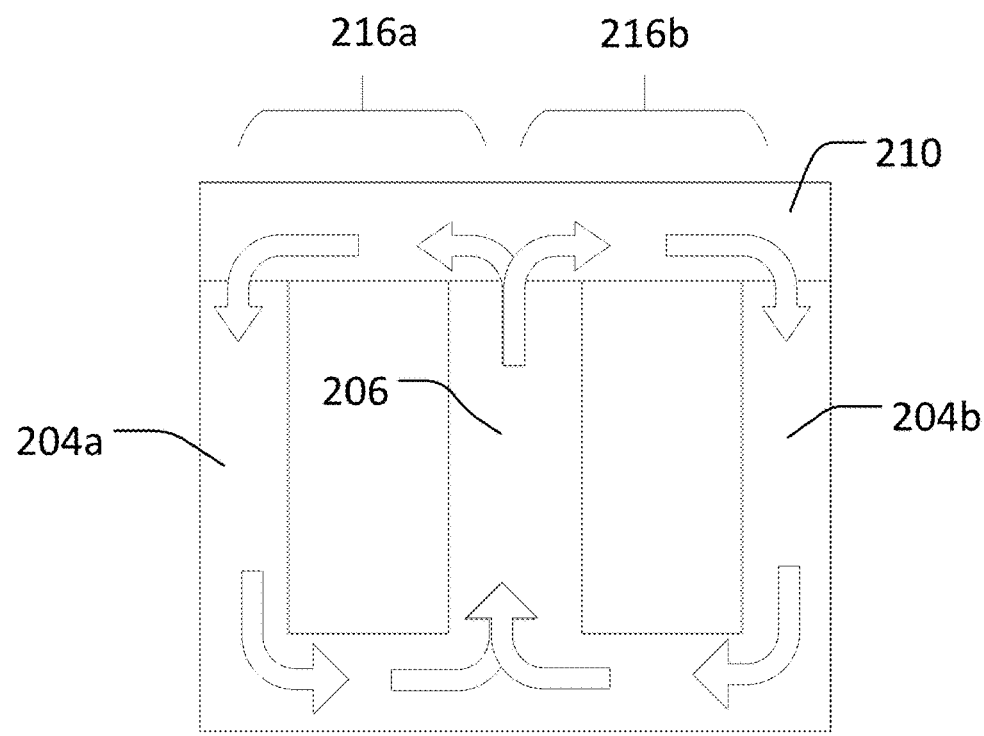

As further illustrated in FIGS. 2C, 7, and 8A-B, the embodiment of a sensor/transducer 200 may include a cross-bar 210, which extends across the width of the E-shaped core 202 from the outermost side of one of the outer arms 204a, 204b to the outermost side of the other of the outer arms 204a, 204b. Notably, the cross-bar 210 may be arranged to make contact with each of the free ends 212a, 212b of the outer arms 204a, 204b and the free end 214 of the middle arm 206. When brought together in this manner, given that the base portion 208 of the E-shaped core 202 and the cross-bar 210 may be generally parallel to each other with the outer arms 204a, 204b and the middle arm 206 extending between them like rungs of a ladder, the composite assembly of the E-shaped core 202 and the cross-bar 210 may be referred to as an ladder-shaped core. Furthermore, in this manner, two separate sub-circuits 216a and 216b, which each function as a magnetic circuit as addressed more fully below, can be formed with the middle branch 206 (also referred to as middle arm) of the E-shaped core 202 common to both sub-circuits 216a and 216b, as illustrated in FIGS. 8A and 8B. Alternatively, magnetic sub-circuits can be formed even with a slight gap present between the cross-bar 210 and the free ends 212a, 212b of the outer arms 204a, 204b and the free end 214 of the middle arm 206.

Although not illustrated, the cross-bar 210 may be embedded in a carrier medium such as a plastic or soft vinyl bar, with cutouts formed at locations along one side of the cross-bar 210 corresponding to locations of the outer arms 204a, 204b and the middle arm 206 of the E-shaped core 202. The carrier member would be thick enough in a direction extending toward the base portion 208 of the E-shaped core 202, and the cutouts would be sized to receive the free ends 212a, 212b, and 214 of the outer arms 204a, 204b and middle arm 206, respectively, with a friction fit, such that the cross-bar 210 could be joined to the E-shaped core 202 generally like a cap, thereby forming the composite ladder-shaped core and establishing the magnetic sub-circuits 216a and 216b. Other arrangements to facilitate connection between the cross-bar 210 and the free ends 212a, 212b, and 214 of the outer arms 204a, 204b and middle arm 206 will, of course, occur to those having skill in the art.

As alluded to above, the E-shaped core 202 and the cross-bar 210 cooperate to form the magnetic sub-circuits 216a and 216b. Therefore, the E-shaped core 202 and the cross-bar 210 may be fabricated from highly magnetically conductive materials, e.g., as laminates formed from material such as Carpenter High Permeability 49 alloy ("Carpenter 49") which is a 48% nickel-iron alloy that has high saturation flux density, high magnetic permeability and low core loss. It will be appreciated that other materials may also be used.

Figure 2A:
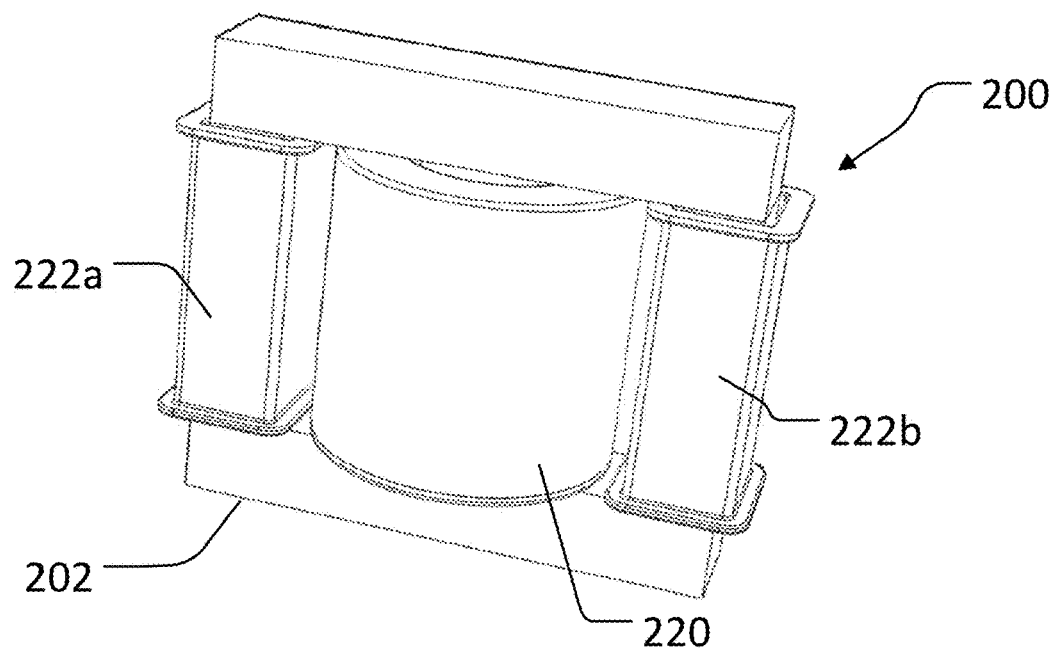
FIGS. 2A and 2B are perspective views from slightly above and from below, respectively, of an embodiment of a sensor/transducer that may be used in a leakage current-management system as illustrated in FIG. 1A.
Figure 2B:
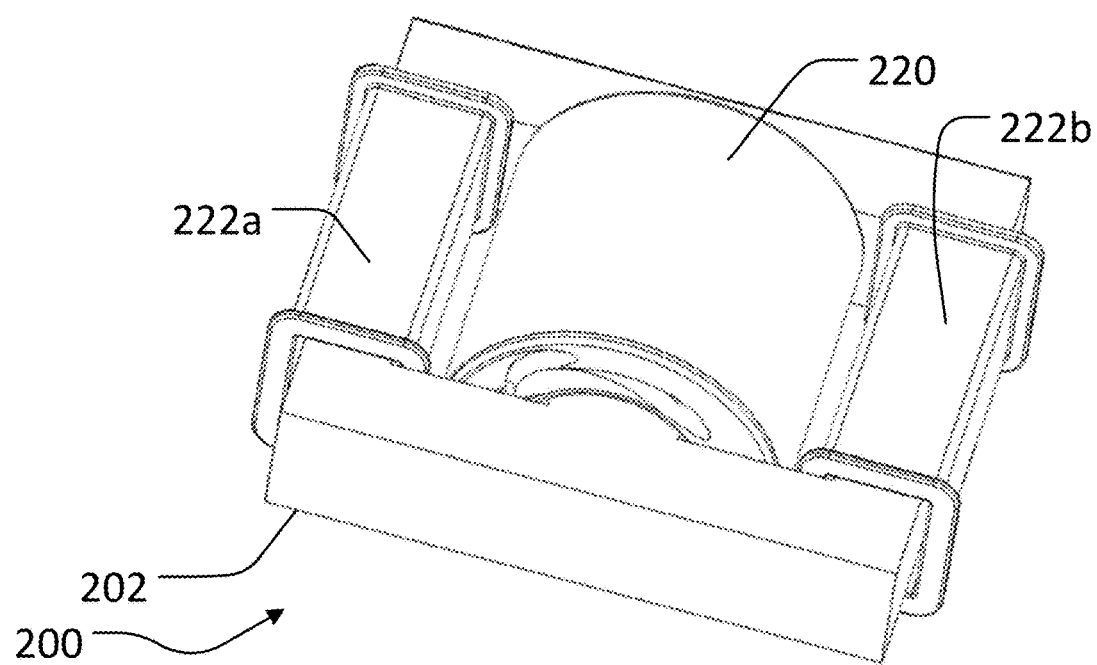
Figure 2C:
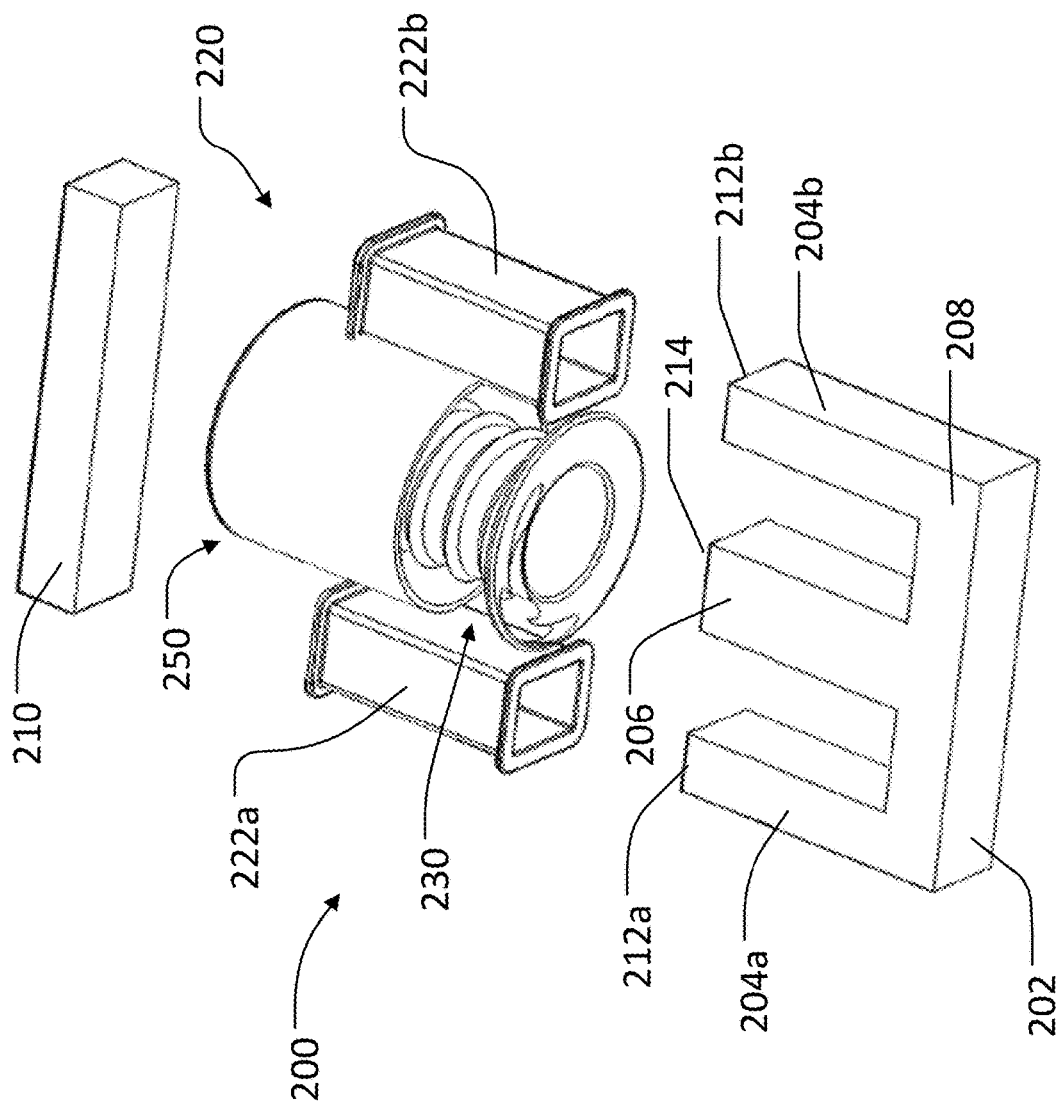
FIG. 2C is an exploded view of the sensor/transducer illustrated in FIGS. 2A and 2B according to embodiments of the disclosed subject matter.

As further illustrated in FIGS. 2A, 2B, and 2C, the sensor/transducer 200 may include a fluid line cassette 220, which slides onto and fits around the middle arm 206 of the E-shaped core 202, and a pair of coil-winding bobbins 222a and 222b, which slide onto and fit around the outer arms 204a, 204b, respectively, of the E-shaped core 202. The fluid line cassette 220 facilitates wrapping a fluid line around the middle arm 206 of the E-shaped core 202 to form a coil, e.g., with on the order of nine or ten loops around the middle arm 206 of the E-shaped core 202, in some embodiments. Suitably, the fluid line cassette 220 may be configured to facilitate double-wrapping of the fluid line 224 around the middle arm 206 of the E-shaped core 202, as illustrated in FIG. 5 and indicated schematically in FIG. 7 and as explained more fully below. Increasing the number of loops of the fluid line 224 enhances sensitivity and resolution of the sensor/transducer 200.

Similarly, as indicated schematically in FIG. 7, the coil-winding bobbins 222a and 222b may each support a large number loops of a conductor such as insulated wire with a conductive core, which is wound into coils 226a and 226b supported on the outer arms 204a, 204b, respectively, of the E-shaped core 202. In embodiments, the core may be made from copper or a copper alloy, and the wire may be of a predetermined wire gauge. As is the case with the fluid line 224, increasing the number of loops of the conductor in each of the coils 226a, 226b enhances sensitivity and resolution of the sensor/transducer 200. The coils 226a and 226b can be connected in series within a sensing circuit (other components of which are not shown), or they can be connected in parallel within the sensing circuit, with the direction of winding (i.e., in the sense of right-hand winding or left-hand winding) being selected accordingly as addressed further below.

Components that can form the fluid line cassette 220 are illustrated in greater detail in FIGS. 3A-E, 4A-B, and 5. These components can include a fluid line spool 230, which is illustrated in FIGS. 3A-E and 5. The fluid line spool 230 can be formed, e.g., from a polymer, such as nylon, polyethylene, or similar, as a generally cylindrical spool tube 232, with a circular flange 234 located at one end of the spool tube 232 and a groove 235 extending around circumferentially around the inner surface of the spool tube 232 at its opposite end. The spool tube may be a part of a fluid line kit, such as a disposable fluid circuit used for dialysis with a length of tubing wrapped around it. In the present context, generally cylindrical includes shapes that do not have a circular cross section, but may have other cross-sectional shapes, such as oval, polygonal, or polygons with rounded vertices. The spool tube 232 is open at both ends to allow the fluid line cassette 220 to fit over the middle arm 206 of the E-shaped core 202, and the internal diameter of the spool tube 232 may be sized for a friction fit—or even a slight interference fit—with the middle arm 206 of the E-shaped core 202.

An external helical thread 236 may be formed on the outer surface of the spool tube 232, extending almost all the way from near the circular flange 234 to the opposite end of the spool tube 232. The "pitch" of the external helical thread 236 may be selected such that the external thread 236 passes around the spool tube 232 on the order of four or five times in total, with sufficient space between successive thread crests for a segment of fluid line 224 to fit between each of a pair of successive thread crests as illustrated in FIG. 3B.

Furthermore, a circumferentially oriented, "double-width" pass-through slot 240 may be formed in the circular flange 234. As illustrated, the pass-through slot 240 is shaped generally like two narrow, circumferentially extending ovals placed side-by-side in the radial direction, with the ovals offset relative to each other in the circumferential direction. As further illustrated, the ends of the ovals may each have a slanted surface, e.g., with the radially inner oval having a slanted surface 242 with a surface normal facing upwardly at one end of the oval and the radially outer oval having a slanted surface 244 with a surface normal facing upwardly at the circumferentially opposite end of the oval. On the other hand, for each of the inner and outer ovals, the respective opposite end of the oval has a slanted surface with a surface normal facing downward, e.g., slanted surface 246 for the radially inner oval and slanted surface 248 for the radially outer oval, as shown in FIG. 3D.

Figure 3E:
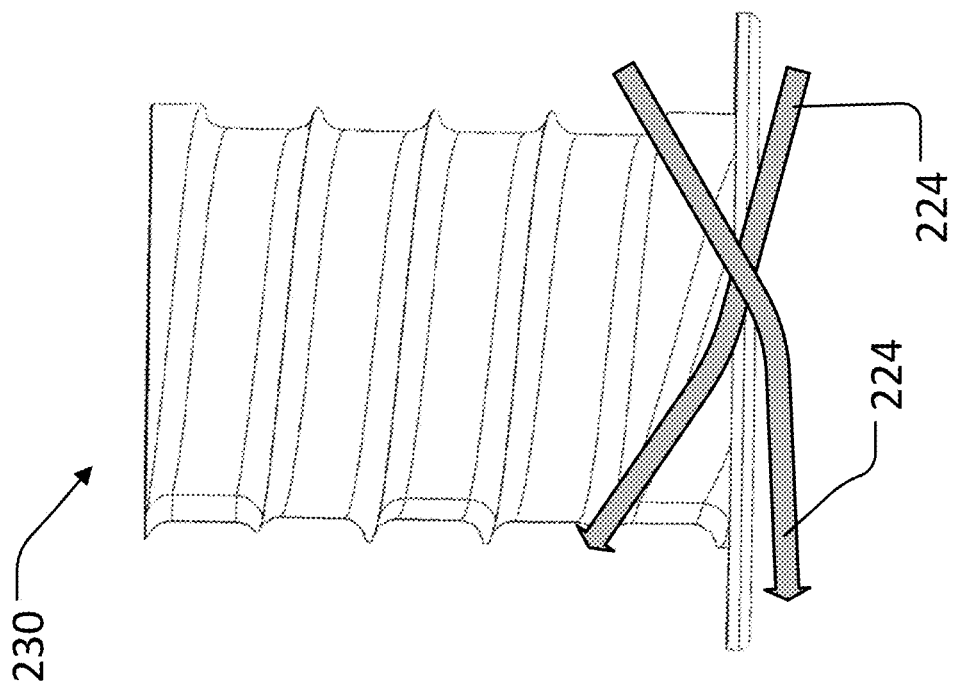
FIG. 3E is side view of the fluid line spool, indicated schematically how the fluid line enters and exits the fluid line spool according to embodiments of the disclosed subject matter.
Figure 3D:
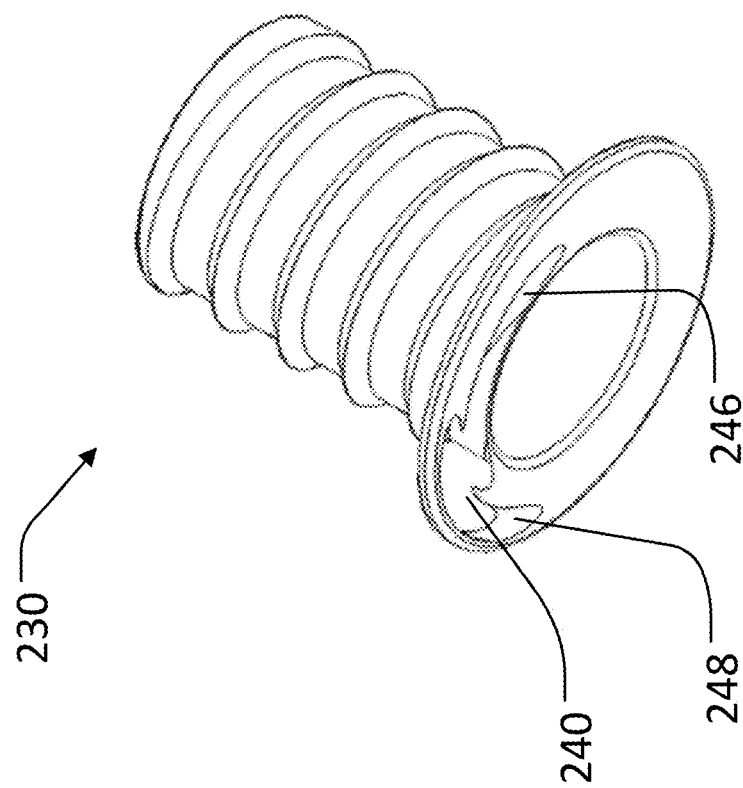
FIG. 3D is a perspective view from below of the fluid line spool according to embodiments of the disclosed subject matter.
Figures 4A, 4B:
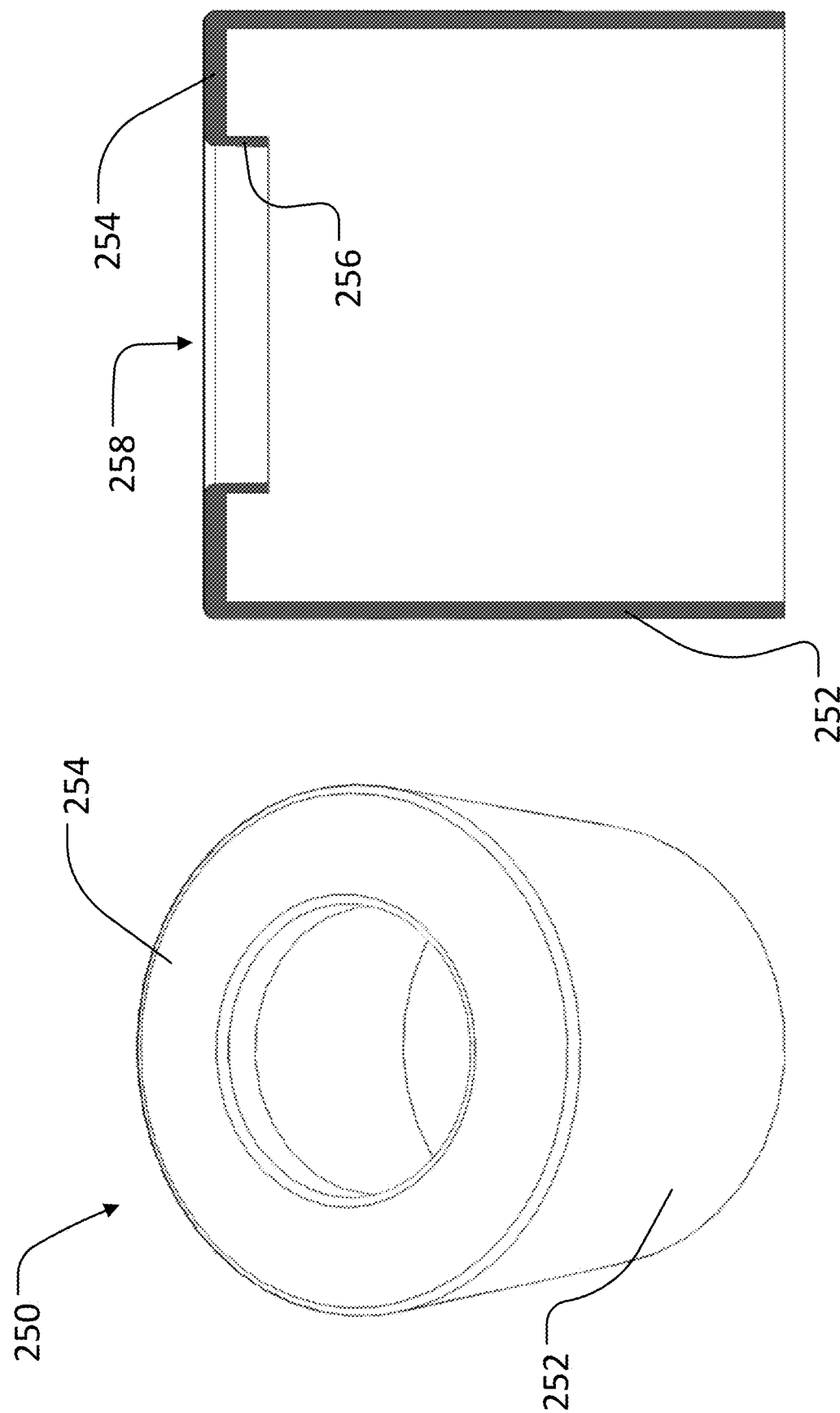
FIGS. 4A and 4B are a perspective view from above and a section view, respectively, of a spool cover that may be used in connection with the fluid line spool illustrated in FIGS. 3A-E to form a fluid line cassette according to embodiments of the disclosed subject matter.

As illustrated in FIGS. 3B and 3E in particular, this configuration makes it possible for a length of fluid line 224 to be inserted through the slot 240 from below (relative to the circular flange 234) via the radially inner oval and helically wound around the length of the spool tube 232 from the flange end of the spool tube 232 to the opposite end of the spool tube 232, with the fluid line 224 located between successive segments of the helical thread 236. The fluid line 224 can then be helically wound "back down" the length of the spool tube 232 and passed back through the pass-through slot 240 via the radially outer oval, with the second "wrap" of the fluid line 224 (not illustrated) overlying the first "wrap" of the fluid line 224, which is the "layer" illustrated in FIG. 3B.

Furthermore, the slanted surfaces 242, 244, 246, and 248 allow the fluid line 224 to lie relatively flush against the upper and lower surfaces of the circular flange 234, with the fluid line 224 passing through the circular flange at a relatively shallow angle, i.e., on the order of 15° or less. As a result, the overall "course" a given fluid line follows between a patient and a medical device, or from one medical device to another medical device, remains essentially unchanged by installation of sensor/transducer 200 onto the fluid line.

To help keep the fluid line 224 wrapped securely around the spool tube 232, which improves sensing and transducing performance (addressed more fully below) by holding the fluid line 224 uniformly close to the spool tube 232, the fluid line cassette 220 can also include a spool cover 250, as illustrated in FIGS. 2C, 4A-B, and 5. The spool cover 250 may be formed, e.g., from plastic or hard nylon, as a relatively thin-walled cylindrical outer wall 252, which is open at its lower end and which has an outer diameter that matches the diameter of the circular flange 234 of the fluid line spool 230. A washer-shaped end wall 254 is located at the upper end of the spool cover 250, with a short length of a cylindrical inner wall 256 surrounding the opening 258 in the middle of the end wall 254. The outer diameter of the cylindrical inner wall 256 matches the diameter of the groove 235 extending around circumferentially around the inner surface of the spool tube 232, and the height of the cylindrical inner wall 256 (in the axial direction of the spool cover 250) matches the height of the groove 235 (in the axial direction of the spool tube 232). The thickness of the cylindrical inner wall 256 can match the depth of the groove 235 (in the radial direction of the spool tube 232). With this configuration, the spool cover 250 can be joined to the fluid line spool 230, with the lower end of the spool cover's outer wall 252 bearing against the circular flange 234 of the fluid line spool 230 and the cylindrical inner wall 256 fitting neatly within the groove 235, as illustrated in FIG. 5. In this manner, the fluid line 224 can be held in a coiled arrangement surrounding the spool tube 232—and surrounding the middle arm 206 of the E-shaped core 202 when the fluid line cassette 220 is installed onto it—with the fluid line 224 residing in an annular chamber 260 formed between the spool tube 230 and the spool cover 250.

In an embodiment, the spool 230 may have a length of tubing bonded to it (e.g. by heat welding or glue, etc.) and the cover 250 may be attached to the spool, such that ends of the bonded tubing protrude out of the combined structure, and have connectors compatible with various medical tubing. In this way, a coiled fluid pathway can be provided for easy use during a medical treatment, without requiring the coiling of tubing around the spool at the time of treatment, but instead at an earlier time, making the treatment itself faster. In other embodiments, a monolithic structure that mimics the shape of a tube coiled around spool 230 can be made by 3-D printing or molding. This monolithic structure has a coiled fluid channel formed in a material, and has two fluid line connectors (e.g., luer type connectors) for easy attachment to a fluid line.

Figure 6C:
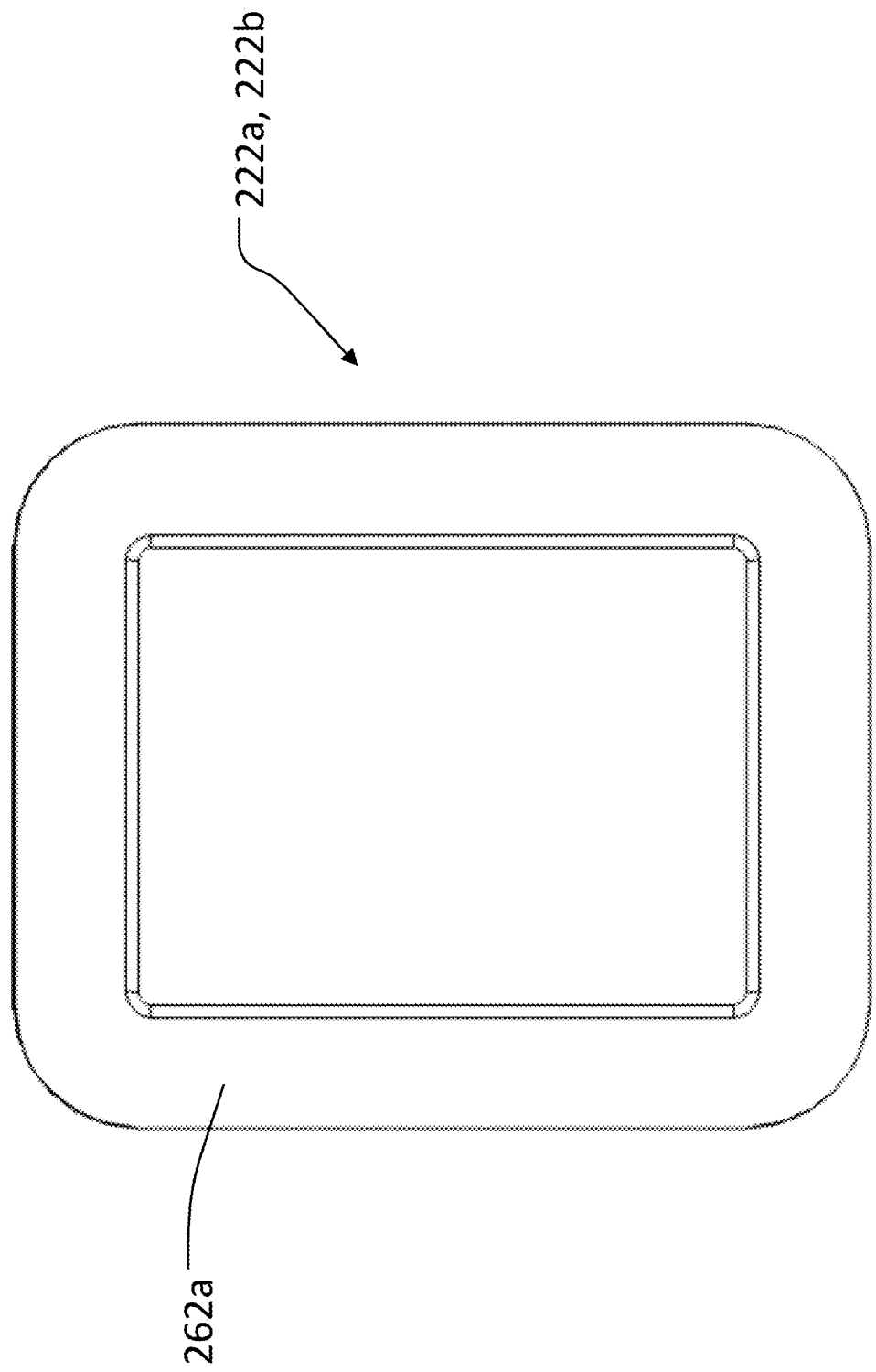
FIG. 6C is a plan view of the coil-winding bobbin according to embodiments of the disclosed subject matter.

As illustrated in FIGS. 6A-C, the coil-winding bobbins 222a, 222b may be formed, e.g., from plastic or hard nylon, with a fairly simple columnar configuration that is open at upper and lower ends. To prevent the coil-winding bobbins 222a, 222b from rotating on the arms of the E-shaped core 202 to which they are mounted, which could cause the electrical conductors that are coiled around the coil-winding bobbins to unspool or perhaps even break, the coil-winding bobbins 222a, 222b may have a non-circular cross-section—e.g. rectangular—that matches the cross-sectional shape of the arms of the E-shaped core to which they are mounted. Flanges 262a and 262b are formed at the upper and lower ends of the coil-winding bobbins 222a, 222b to prevent the conductor coils 226a and 226b from sliding off of the coil-winding bobbins.

In general, the sensor/transducer 200 operates in accordance with the same principles. Current flowing within the coils of the fluid line 224, carried by the conductive fluid being transported by the fluid line, establishes a magnetic field that extends locally along the middle arm 206 of the core. The direction in which the magnetic field extends along the middle arm 206 of the core depends on the direction in which the current is flowing within the fluid line coils, in accordance with a right-hand rule, and the strength of the magnetic field will be proportional to the number of coils that are wrapped around the middle arm 206 of the core. Magnetic flux will, in turn, extend along the magnetic sub-circuits 216a and 216b, as illustrated in FIGS. 8A and 8B, with the direction of circulation likewise depending on the direction in which the electrical current is flowing relative to the middle arm 206 of the core.

For direct current (DC) flowing within the fluid line coils, the magnetic fields will be constant, and there will be no effect on the conductor coils 226a and 226b located on the outer arms 204a, 204b of the core. On the other hand, if alternating current (AC) flows within the fluid line coils, the magnitude and direction of the magnetic field established by the current and extending along the middle arm 206 of the core will vary sinusoidally with the alternating current, as will the magnitude and direction of the magnetic flux extending along the magnetic sub-circuits 216a and 216b as illustrated schematically in FIGS. 8A and 8B. Furthermore, as the magnetic flux passing through the conductor coils 226a and 226b varies in magnitude and direction, voltages (emf) will be induced across the conductor coils in accordance with Faraday's law of induction. The magnitude of the induced voltage in each of the conductor coils 226a, 226b will be proportional to the time rate of change in magnetic flux through the given conductor coil as well as the number of loops in the given coil. Additionally, the ratio of the voltage induced across a conductor coil to the voltage drop across the fluid line coils (associated with current flowing along the coiled length of the fluid line) will be the same as the ratio of the number of loops in a conductor coil to the number of loops in the fluid line coil. Furthermore, the induced voltage will act in a direction that causes induced current to flow along the conductor coil in a direction such that the magnetic field associated with the induced current opposes the time-varying nature of the magnetic flux through the coil, in accordance with Lenz's law. Thus, by measuring the induced voltage across the conductor coils 226a, 226b, knowing the ratio of the number of conductor coil turns to the number of fluid line loops in the fluid line coil, and using a predetermined value of resistance through fluid along the coiled length of the fluid line, the amount of current flowing along the coiled length of the fluid line can be ascertained based on the formula i=V/R.

Alternatively, the sensor/transducer 200 can be used to counteract leakage current flowing within the fluid line, as alluded to above, by applying appropriate voltage to the conductor coils 226a, 226b. In particular, by applying a voltage across the conductor coils 226a, 226b, the electromagnetic principles explained above (Faraday's law and Lenz's law) will operate "in the reverse direction" to induce a voltage potential across the coiled length of fluid line, with attendant induced current in the fluid line. Thus, if the amount and direction of leakage current in the fluid line is detected (e.g., by measuring it using a proximal current sensor 108 located upstream of the current-cancelling transducer 116 and/or a distal current sensor 118 located downstream of the current-cancelling transducer 116) so that the amount of induced current that needs to be injected into the fluid line is known, then the amount of voltage to be applied to the conductor coils 226a, 226b can be determined using the same principles as those described immediately above.

As noted above, the conductor coils 226a and 226b can be connected in series within a sensing circuit or they can be connected in parallel within the sensing circuit, and the direction of winding should be selected accordingly. In particular, as illustrated in FIGS. 8A and 8B, the magnetic flux in each of the outer arms 204a and 204b flows in the same direction relative to the base portion 208 of the E-shaped core 202. Therefore, if the conductor coils 206a and 206b are connected in series, they can be installed onto the outer arms 204a and 204b inverted relative to each other so that the direction of advance of the loops of one of the coils (e.g., using a right-hand rule) is, for example, from the base portion 208 toward the cross-bar 210 and the direction of advance of the loops of the other coil is from the cross-bar 210 to the base portion 208. With this arrangement, the magnetic fields associated with current flowing along the conductor coils 206a and 206b in series will be aligned in the same direction as each other (base portion 208 to cross-bar 210 or vice-versa), which prevents counter-acting or cancelling flows of magnetic flux along the middle arm 206 of the core.

On the other hand, if the conductor coils 206a and 206b are connected in parallel, they can be installed onto the outer arms 204a and 204b with the direction of advance of their respective being the same, i.e., both extending from the base portion 208 of the E-shaped core toward the cross-bar 210 or vice-versa. With this arrangement, current flowing simultaneously through the conductor coils 206a, 206b (i.e., in parallel) will generate associated magnetic fields that are co-aligned so as not to produce counter-acting or cancelling flows of magnetic flux along the middle arm 206 of the core.

According to a first further embodiment, there is provided a device for detecting an electrical current flowing through a fluid line, comprising a magnetically conductive core with a centrally located support member configured to receive a length of coiled conductor, and at least two electrically conducting coils located at positions that are spaced from the centrally located support member on opposite sides thereof. The magnetically conductive core comprises a magnetically conductive central branch on which the centrally located support member is disposed in surrounding relationship and a pair of magnetically conductive outer branches with at least one of the electrically conducting coils disposed in surrounding relationship to each of the outer branches.

According to a second further embodiment, there is provided the device of the first further embodiment, wherein the magnetically conductive core forms two magnetic sub-circuits with the magnetically conductive central branch forming a common portion of each of the two magnetic sub-circuits and with each of the magnetically conductive outer branches forming a portion of one of the two magnetic sub-circuits.

According to a third further embodiment, there is provided the device of the first further embodiment, wherein the conductor is a hollow tube filled with an electrically conductive fluid.

According to a fourth further embodiment, there is provided the device of the third further embodiment, wherein the hollow tube is made of an electrically insulating material.

According to a fifth further embodiment, there is provided the device of the fourth further embodiment, wherein the electrically insulating material includes a polymer.

According to a sixth further embodiment, there is provided the device of the third further embodiment, wherein the hollow tube is made of a semi-conductive material.

According to a seventh further embodiment, there is provided the device of the sixth further embodiment, wherein the semi-conductive material includes carbon impregnated polymer.

According to an eighth further embodiment, there is provided the device of the seventh further embodiment, wherein the carbon impregnated polymer includes polyvinylchloride.

According to a ninth further embodiment, there is provided the device of the first further embodiment, wherein the magnetically conductive core comprises a ladder-shaped core.

According to a tenth further embodiment, there is provided the device of the ninth further embodiment, wherein the ladder-shaped core comprises a magnetically conductive E-shaped core member and a magnetically conductive cross-bar.

According to an eleventh further embodiment, there is provided the device of the tenth further embodiment, wherein the magnetically conductive E-shaped core member forms the magnetically conductive central branch and the magnetically conductive outer branches and wherein the magnetically conductive cross-bar is removably connectable to free ends of the magnetically conductive central branch and the magnetically conductive outer branches.

According to a twelfth further embodiment, there is provided the device of the first further embodiment, wherein the centrally located support member comprises a spool which surrounds the magnetically conductive central branch.

According to a thirteenth further embodiment, there is provided the device of the twelfth further embodiment, wherein the spool has an external helical thread, and the thread has a size that accommodates the tube conveying conductive fluid, such that the tube fits tightly into the treads.

According to a fourteenth further embodiment, there is provided the device of the twelfth further embodiment, wherein the spool comprises an externally helically threaded central spool tube and a circular flange located at an end thereof.

According to a fifteenth further embodiment, there is provided the device of the fourteenth further embodiment, wherein the circular flange has a circumferentially oriented pass-through slot that is generally adjacent to the central spool tube.

According to a sixteenth further embodiment, there is provided the device of the fifteenth further embodiment, wherein the pass-through slot is formed as a pair of circumferentially extending ovals that are positioned side-by-side and that are circumferentially shifted relative to each other.

According to a seventeenth further embodiment, there is provided the device of the sixteenth further embodiment, wherein ends of the circumferentially extending ovals are slanted to facilitate passage of tubing through the pass-through slot at an angle of 15° or less relative to a plane in which the circular flange lies.

According to an eighteenth further embodiment, there is provided the device of the fourteenth further embodiment, wherein the centrally located support member comprises a cassette comprising the spool and a spool cover configured to mate with the spool, defining an annular chamber surrounding the externally helically threaded central spool tube.

According to a nineteenth further embodiment, there is provided the device of the fourteenth further embodiment, wherein the electrically conducting coils are supported by respective bobbins.

According to a twentieth further embodiment, there is provided a system for sensing and counteracting leakage current from a patient fluidly connected to a medical device by tubing filled with a conductive fluid. The system comprises at least a pair of sensor/transducers, each of the sensor/transducers including a magnetically conductive core with a centrally located support member configured to receive a length of tubing filled with the conductive fluid, and at least two electrically conducting coils located at positions that are spaced from the centrally located support member on opposite sides thereof. The magnetically conductive core comprises a magnetically conductive central branch on which the centrally located support member is disposed in surrounding relationship and a pair of magnetically conductive outer branches with at least one of the electrically conducting coils disposed in surrounding relationship to each of the outer branches. The magnetically conductive core forms two magnetic sub-circuits with the magnetically conductive central branch forming a common portion of each of the two magnetic sub-circuits and with each of the magnetically conductive outer branches forming a portion of one of the two magnetic sub-circuits. The at least a pair of sensor/transducers are disposed on the tubing with the tubing supported by the centrally located support member and coiled around the magnetically conductive central branch of each sensor/transducer, with a first one of the sensor/transducers arranged to detect leakage current flowing within the conductive fluid and a second one of the sensor/transducers arranged to induce current within the conductive fluid to counteract the leakage current when voltage is applied to the electrically conducting coils of the second sensor/transducer.

It is, thus, apparent that there is provided, in accordance with the present disclosure, system and method for reducing current flowing in a conductive fluid. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present disclosure.

What is claimed is:

1. A device for detecting an electrical current flowing through a fluid line, the device comprising:
    a magnetically conductive core with a centrally located support member configured to receive a length of coiled conductor, and
    at least two electrically conducting coils located at positions that are spaced from the centrally located support member on opposite sides thereof, wherein
    the magnetically conductive core comprises a magnetically conductive central branch on which the centrally located support member is disposed in surrounding relationship and a pair of magnetically conductive outer branches with at least one of the electrically conducting coils disposed in surrounding relationship to each of the outer branches, and
    the centrally located support member comprises a spool which surrounds the magnetically conductive central branch.

2. The device according to claim 1, wherein the magnetically conductive core forms two magnetic sub-circuits with the magnetically conductive central branch forming a common portion of each of the two magnetic sub-circuits and with each of the magnetically conductive outer branches forming a portion of one of the two magnetic sub-circuits.

3. The device according to claim 1, wherein the conductor is a hollow tube filled with an electrically conductive fluid.

4. The device according to claim 3, wherein the hollow tube is made of an electrically insulating material.

5. The device according to claim 4, wherein the electrically insulating material includes a polymer.

6. The device according to claim 3, wherein the hollow tube is made of a semi-conductive material.

7. The device according to claim 6, wherein the semi-conductive material includes carbon impregnated polymer.

8. The device according to claim 7, wherein the carbon impregnated polymer includes polyvinylchloride.

9. The device according to claim 1, wherein the magnetically conductive core comprises a ladder-shaped core.

10. The device according to claim 9, wherein the ladder-shaped core comprises a magnetically conductive E-shaped core member and a magnetically conductive cross-bar.

11. The device according to claim 10, wherein the magnetically conductive E-shaped core member forms the magnetically conductive central branch and the magnetically conductive outer branches and wherein the magnetically conductive cross-bar is removably connectable to free ends of the magnetically conductive central branch and the magnetically conductive outer branches.

12. The device according to claim 1, wherein the spool has an external helical thread.

13. The device according to claim 1, wherein the spool comprises an externally helically threaded central spool tube and a circular flange located at an end thereof.

14. The device according to claim 13, wherein the circular flange has a circumferentially oriented pass-through slot that is generally adjacent to the central spool tube.

15. The device according to claim 14, wherein the pass-through slot is formed as a pair of circumferentially extending ovals that are positioned side-by-side and that are circumferentially shifted relative to each other.

16. The device according to claim 15, wherein ends of the circumferentially extending ovals are slanted to facilitate passage of tubing through the pass-through slot at an angle of 15° or less relative to a plane in which the circular flange lies.

17. The device according to claim 13, wherein the centrally located support member comprises a cassette comprising the spool and a spool cover configured to mate with the spool, defining an annular chamber surrounding the externally helically threaded central spool tube.

18. The device according to claim 13, wherein the electrically conducting coils are supported by respective bobbins.

19. A system for sensing and counteracting leakage current from a patient fluidly connected to a medical device by tubing filled with a conductive fluid, the system comprising:
    at least a pair of sensor/transducers, each of the sensor/transducers including
    a magnetically conductive core with a centrally located support member configured to receive a length of tubing filled with the conductive fluid, and
    at least two electrically conducting coils located at positions that are spaced from the centrally located support member on opposite sides thereof,
    wherein the magnetically conductive core comprises a magnetically conductive central branch on which the centrally located support member is disposed in surrounding relationship and a pair of magnetically conductive outer branches with at least one of the electrically conducting coils disposed in surrounding relationship to each of the outer branches, and wherein the magnetically conductive core forms two magnetic sub-circuits with the magnetically conductive central branch forming a common portion of each of the two magnetic sub-circuits and with each of the magnetically conductive outer branches forming a portion of one of the two magnetic sub-circuits, wherein said at least a pair of sensor/transducers are disposed on the tubing with the tubing supported by the centrally located support member and coiled around the magnetically conductive central branch of each sensor/transducer, with a first one of the sensor/transducers arranged to detect leakage current flowing within the conductive fluid and a second one of the sensor/transducers arranged to induce current within the conductive fluid to counteract the leakage current when voltage is applied to the electrically conducting coils of the second sensor/transducer.

* * * * *